United States Patent
Jofuku

(10) Patent No.: US 7,126,043 B1
(45) Date of Patent: Oct. 24, 2006

(54) ADC POLYNUCLEOTIDES AND POLYPEPTIDES, USES THEREOF INCLUDING METHODS FOR IMPROVING SEEDS

(75) Inventor: K. Diane Jofuku, Oak Park, CA (US)

(73) Assignee: Ceres, Inc., Thousand Oaks, CA (US)

( * ) Notice: Subject to any disclaimer, the term of this patent is extended or adjusted under 35 U.S.C. 154(b) by 0 days.

(21) Appl. No.: 09/959,625

(22) PCT Filed: Feb. 25, 2000

(86) PCT No.: PCT/US00/04718

§ 371 (c)(1),
(2), (4) Date: Sep. 5, 2002

(87) PCT Pub. No.: WO00/50585

PCT Pub. Date: Aug. 31, 2000

Related U.S. Application Data

(60) Provisional application No. 60/121,693, filed on Feb. 25, 1999.

(51) Int. Cl.
*C12N 15/82* (2006.01)
*C12N 15/90* (2006.01)
*C12N 15/29* (2006.01)
*A01H 5/00* (2006.01)
*A01H 5/10* (2006.01)

(52) U.S. Cl. .................. 800/290; 435/320.1; 435/468; 536/23.6; 800/285; 800/286; 800/287; 800/298

(58) Field of Classification Search ............ 435/320.1, 435/419, 468; 536/23.6; 800/260, 278, 800/281, 284, 285, 286, 287, 290, 295, 298, 800/306, 317
See application file for complete search history.

(56) References Cited

U.S. PATENT DOCUMENTS 5,994,622 A * 11/1999 Jofuku et al. ............... 800/260
6,093,874 A * 7/2000 Jofuku et al. ............... 800/260
6,329,567 B1 * 12/2001 Jofuku et al. ............... 800/260
6,846,669 B1 * 1/2005 Jofuku et al. ............ 435/320.1
2004/0137466 A1  7/2004 Jofuku et al.

FOREIGN PATENT DOCUMENTS

WO    WO 98/07842    *  2/1998
WO    WO 00/40694 A2    7/2000
WO    WO 99/41974 A1    7/2000

OTHER PUBLICATIONS

Moose, Stephen et al., "Glossy15, an APETALA2-like gene from maize . . . ," Genes & Development, vol. 10, pp. 3018-3027.XP-000989661. (1996).

Riechmann, Jose L. et al., "The AP2/EREBP Family of Plant Transcription Factors," Biol. Chem, vol. 379, Jun. 1998, pp. 633-646. XP002937907.

Chuck, G. et al., "The control of maize spikelet meristem fate . . . ," Database EMBL 'Online!, 1998. XP-002349618.Accession No. AF048900.1.

Allen, R.L. et al., "A barley gene of the APETALA2 family . . . " NCBI Web Database, Accession AAL50205. GI: 18476518. (Feb. 1, 2002).

NCBI Web Database. Accession XM_470121. GI: 50919448 (Nov. 9, 2004).

* cited by examiner

*Primary Examiner*—Ashwin Mehta
(74) *Attorney, Agent, or Firm*—Birch, Stewart, Kolasch & Birch, LLP

(57) ABSTRACT

The invention provides methods of modulating seed mass and other traits in plants, including oat, wheat, rice, and maize. The methods involve producing transgenic plants comprising a recombinant expression cassette containing an ADC nucleic acid linked to a plant promoter.

51 Claims, No Drawings

SEQUENCE LISTING

```
<160> NUMBER OF SEQ ID NOS: 8

<210> SEQ ID NO 1
<211> LENGTH: 489
<212> TYPE: DNA
<213> ORGANISM: Oat ADC Gene

<400> SEQUENCE: 1
tacctaggtg agctcaaatt cccagctcca gctcctccta attaatttcc atctgttctg        60
tgtactgaag ttatttaatt tcgtcaggtg gtttcgacac cgcgcactcg gccgcgaggt       120
tataattaat caagcttcct agtttgaact ttcaacacat actgctctct ctcgattgga       180
ttgtactagc atcatgaact gtactgaaac gggtcttgct cagggcctac gatcgcgcgg       240
cgatcaagtt ccggggactg gacgccgaca tcaacttcaa tctgagcgac tacgaggagg       300
atctgaagca ggtaactgaa taagatcgct tcctcaaatg cagcatagat attatcggtg       360
tgtgtgtgtc tgatgggtgg ttggtggccg gccgggcact cttgttttg ccagatgagg        420 aactggacca aggaggagtt cgtgcacatc ctccgccgcc agagcacggg gttcgcgagg       480
gggagctca                                                              489

<210> SEQ ID NO 2
<211> LENGTH: 65
<212> TYPE: PRT
<213> ORGANISM: Oat ADC Protein

<400> SEQUENCE: 2

Gly Gly Phe Asp Thr Ala His Ser Ala Ala Arg Ala Tyr Asp Arg Ala
1               5                   10                  15

Ala Ile Lys Phe Arg Gly Leu Asp Ala Asp Ile Asn Phe Asn Leu Ser
            20                  25                  30

Asp Tyr Glu Glu Asp Leu Lys Gln Val Thr Asn Trp Thr Lys Glu Glu
        35                  40                  45

Phe Val His Ile Leu Arg Arg Gln Ser Thr Gly Phe Ala Arg Gly Ser
    50                  55                  60

Ser
65

<210> SEQ ID NO 3
<211> LENGTH: 387
<212> TYPE: DNA
<213> ORGANISM: Rice ADC Gene

<400> SEQUENCE: 3
cctaggtaat ttcatcgaac acatcatctt cctcctctca atccaacgcg acatcgccat        60
gaacaatcta acaaacacct tcatcttctc ccaaacaatc acaggtggat tcgacactgc       120
```

-continued

```
tcacgcagct gcaaggtaaa gaacacatca catcattcat cagaacatga gctctgtgtt      180
tgtgaaggag attgagagaa ttgaatgatg atggatggat gcaggcgta cgacagggcg       240 gcgatcaagt tcaggggagt agaggctgac atcaacttca acctgagcga ctacgaggag      300
gacatgaggc agatgaagag cttgtccaag gaggagttcg tgcacgttct ccggcgacag      360
agcaccggct tctcccgcgg cagctca                                          387
```

<210> SEQ ID NO 4
<211> LENGTH: 65
<212> TYPE: PRT
<213> ORGANISM: Rice ADC Protein

<400> SEQUENCE: 4

```
Gly Gly Phe Asp Thr Ala His Ala Ala Ala Arg Ala Tyr Asp Arg Ala
1               5                   10                  15

Ala Ile Lys Phe Arg Gly Val Glu Ala Asp Ile Asn Phe Asn Leu Ser
            20                  25                  30

Asp Tyr Glu Glu Asp Met Arg Gln Met Lys Ser Leu Ser Lys Glu Glu
        35                  40                  45

Phe Val His Val Leu Arg Arg Gln Ser Thr Gly Phe Ser Arg Gly Ser
    50                  55                  60

Ser
65
```

<210> SEQ ID NO 5
<211> LENGTH: 477
<212> TYPE: DNA
<213> ORGANISM: Wheat ADC Gene

<400> SEQUENCE: 5

```
cttgggtggg tttgacactg cacatgctgc tgcaaggtac gtacaaattt aattaagcac      60
gtacgcagta cataattgtg atgtgatcat caccctgaacc acctgtactg caactctgaa    120
gttatgtctc cactctgttc atttcaccgt gccaaattga ccttgggatg ttccgcaggg     180
cgtacgatcg agcggcgatc aagttccgcg gcgtcgacgc cgacataaac ttcaacctca    240
gcgactacga ggacgacatg aagcaggtga tcagcaaagc caccaaccag tgttcctcat    300
ccaaccaaat tattcagatg cagagtgcat tagtactgtt gttgaaactg atgaactgaa    360
gaaattctga ctgtgtgttg kttggtggat gatctggatc agatgaaggg cctgtccaag    420
gaggagttcg tgcacgtgct gcggcggcag agcgccggct tctcgcgggg cagctcc       477
```

<210> SEQ ID NO 6
<211> LENGTH: 65
<212> TYPE: PRT
<213> ORGANISM: Wheat ADC Protein

<400> SEQUENCE: 6

```
Gly Gly Phe Asp Thr Ala His Ala Ala Ala Arg Ala Tyr Asp Arg Ala
1               5                   10                  15

Ala Ile Lys Phe Arg Gly Val Asp Ala Asp Ile Asn Phe Asn Leu Ser
            20                  25                  30

Asp Tyr Glu Asp Asp Met Lys Gln Val Lys Gly Leu Ser Lys Glu Glu
        35                  40                  45

Phe Val His Val Leu Arg Arg Gln Ser Ala Gly Phe Ser Arg Gly Ser
    50                  55                  60

Ser
65
```

```
<210> SEQ ID NO 7
<211> LENGTH: 489
<212> TYPE: DNA
<213> ORGANISM: Maize ADC Gene

<400> SEQUENCE: 7
cttaggtgag cagcaataag cagatcgatc tgcagcataa atttcccgtt attaactagt      60
tcgtgatctc gatcgaatgg cctaattaac cgattcggtg atctggccga tggccaatct     120
acgcaggtgg attcgacact gctcatgccg ctgcaaggta acgatcaatc catccatcca     180
cccttgtcta gctacccac cgaccggccg gattaatgga ccgctagttc tcgggacggg      240
cttgctgcag ggcgtacgac cgagcggcga tcaagttccg cggcgtcgac gccgacataa     300
acttcaacct cagcgactac gacgacgata tgaagcaggt acatacacga gtgttgttgc     360
agctagcacc gactgaaaca tctgctgaac gtacactcat ggcctgtgca ccagatgaag     420
agcctgtcca aggaggagtt cgtgcacgcc ctgcggcggc agagcaccgg cttctcccgt     480
ggcagctcc                                                             489

<210> SEQ ID NO 8
<211> LENGTH: 65
<212> TYPE: PRT
<213> ORGANISM: Maize ADC Protein

<400> SEQUENCE: 8

Gly Gly Phe Asp Thr Ala His Ala Ala Ala Arg Ala Tyr Asp Arg Ala
1               5                   10                  15

Ala Ile Lys Phe Arg Gly Val Asp Ala Asp Ile Asn Phe Asn Leu Ser
            20                  25                  30

Asp Tyr Asp Asp Asp Met Lys Gln Val Lys Ser Leu Ser Lys Glu Glu
        35                  40                  45

Phe Val His Ala Leu Arg Arg Gln Ser Thr Gly Phe Ser Arg Gly Ser
    50                  55                  60

Ser
65
```

ADC POLYNUCLEOTIDES AND POLYPEPTIDES, USES THEREOF INCLUDING METHODS FOR IMPROVING SEEDS

This application is a national phase under 35 U.S.C § 371 of PCT International Application No. PCT/US00/04718 which has an International filing date of Feb. 25, 2000, which designated the United States of America. This application also claims priority to U.S. Provisional Application No. 60/121,693, filed on Feb. 25, 1999.

FIELD OF THE INVENTION

The present invention is directed to plant genetic engineering. In particular, it relates to new methods for modulating mass and other properties of plant seeds.

BACKGROUND OF THE INVENTION

The pattern of flower development is controlled by the floral meristem, a complex tissue whose cells give rise to the different organ systems of the flower. Genetic and molecular studies have defined an evolutionarily conserved network of genes that control floral meristem identity and floral organ development in *Arabidopsis*, snapdragon, and other plant species (see, e.g., Coen and Carpenter, *Plant Cell* 5:1175–1181 (1993) and Okamuro et al., Plant Cell 5:1183–1193 (1993)). In *Arabidopsis*, a floral homeotic gene APETALA2 (AP2) controls three critical aspects of flower ontogeny—the establishment of the floral meristem (Irish and Sussex, *Plant Cell* 2:741–753 (1990); Huala and Sussex, *Plant Cell* 4:901–913 (1992); Bowman et al., *Development* 119:721–743 (1993); Schultz and Haughn, *Development* 119:745–765 (1993); Shannon and Meeks-Wagner, *Plant Cell* 5:639–655 (1993)), the specification of floral organ identity (Komaki et al., *Development* 104:195–203 (1988)); Bowman et al., *Plant Cell* 1:37–52 (1989); Kunst et al., *Plant Cell* 1:1195–1208 (1989)), and the temporal and spatial regulation of floral homeotic gene expression (Bowman et al., *Plant Cell* 3:749–758 (1991); Drews et al., *Cell* 65:91–1002 (1991)).

One early function of AP2 during flower development is to promote the establishment of the floral meristem. AP2 performs this function in cooperation with at least three other floral meristem genes, APETALA1 (AP1), LEAFY (LFY), and CAULIFLOWER (CAL) (Irish and Sussex (1990); Bowman, *Flowering Newsletter* 14:7–19 (1992); Huala and Sussex (1992); Bowman et al., (1993); Schultz and Haughn, (1993); Shannon and Meeks-Wagner, (1993)). A second function of AP2 is to regulate floral organ development. In *Arabidopsis*, the floral meristem produces four concentric rings or whorls of floral organs—sepals, petals, stamens, and carpels. In weak, partial loss-of-function ap2 mutants, sepals are homeotically transformed into leaves, and petals are transformed into pollen-producing stamenoid organs (Bowman et al., *Development* 112:1–20 (1991)). By contrast, in strong ap2 mutants, sepals are transformed into ovule-bearing carpels, petal development is suppressed, the number of stamens is reduced, and carpel fusion is often defective (Bowman et al., (1991)). Finally, the effects of ap2 on floral organ development are in part a result of a third function of AP2, which is to directly or indirectly regulate the expression of several flower-specific homeotic regulatory genes (Bowman et al., *Plant Cell* 3:749–758 (1991); Drews et al., *Cell* 65:91–1002 (1991); Jack et al. *Cell* 68:683–697 (1992); Mandel et al. *Cell* 71: 133–143 (1992)).

Clearly, Ap2 plays a critical role in the regulation of *Arabidopsis* flower development. Yet, little is known about how it carries out its functions at the cellular and molecular levels. A spatial and combinatorial model has been proposed to explain the role of AP2 and other floral homeotic genes in the specification of floral organ identity (see, e.g., Coen and Carpenter, supra). One central premise of this model is that AP2 and a second floral homeotic gene AGAMOUS (AG) are mutually antagonistic genes. That is, AP2 negatively regulates AG gene expression in sepals and petals, and conversely, AG negatively regulates AP2 gene expression in stamens and carpels. In situ hybridization analysis of AG gene expression in wild-type and ap2 mutant flowers has demonstrated that AP2 is indeed a negative regulator of AG expression. However, it is not yet known how AP2 controls AG. Nor is it known how AG influences AP2 gene activity.

The AP2 gene in *Arabidopsis* has been isolated by T-DNA insertional mutagenesis as described in Jofuku et al. *The Plant Cell* 6:1211–1225 (1994). AP2 encodes a putative nuclear factor that bears no significant similarity to any known fungal, or animal regulatory protein.

SUMMARY OF THE INVENTION

The present invention relates to AP2 domain containing ("ADC") polynucleotides and polypeptides, including variants thereof, such as mutants, fragments, and fusions. Such polynucleotides of the invention can be used to construct ribozyme, antisense, and expression constructs and vectors. Also, within the scope of the invention are host cells comprising these constructs and vectors to modulate expression of ADC polypeptides in any number of cell types, including, without limitation, bacterial, yeast, insect, mammalian, and plant.

The present invention provides methods of modulating seed mass and other traits in plants, such as oat, wheat, rice, and maize, for example. The methods involve providing a plant comprising a recombinant expression cassette containing an ADC nucleic acid linked to a plant promoter. The plant is either selfed or crossed with a second plant to produce a plurality of seeds. Seeds with the desired trait (e.g., altered mass) are then selected.

In some embodiments, transcription of the ADC nucleic acid inhibits expression of an endogenous ADC gene or activity the encoded protein. In these embodiments, the step of selecting includes the step of selecting seed with increased mass or another trait. The seed may have, for instance, increased protein content, carbohydrate content, or oil content. In the case of increased oil content, the types of fatty acids may or may not be altered as compared to the parental lines. In these embodiments, the ADC nucleic acid may be linked to the plant promoter in the sense or the antisense orientation. Alternatively, expression of the ADC nucleic acid may enhance expression of an endogenous ADC gene or ADC activity and the step of selecting includes the step of selecting seed with decreased mass. This embodiment is particularly useful for producing seedless varieties of crop plants.

If the first plant is crossed with a second plant the two plants may be the same or different species. The plants may be any higher plants, for example, members of the families Brassicaceae or Solanaceae. In making seed of the invention, either the female or the male parent plant can comprise the expression cassette containing the ADC nucleic acid. In preferred embodiments, both parents contain the expression cassette.

In the expression cassettes, the plant promoter may be a constitutive promoter, for example, the CaMV 35S promoter. Alternatively, the promoter may be a tissue-specific promoter. Examples of tissue specific expression useful in the invention include fruit-specific, seed-specific (e.g., ovule-specific, embryo-specific, endosperm-specific, integument-specific, or seed coat-specific) expression.

The invention also provides seed produced by the methods described above. The seed of the invention comprise a recombinant expression cassette containing an ADC nucleic acid. If the expression cassette is used to inhibit expression of endogenous ADC expression, the seed will have a mass at least about 20% greater than the average mass of seeds of the same plant variety which lack the recombinant expression cassette. If the expression cassette is used to enhance expression of ADC, the seed will have a mass at least about 20% less than the average mass of seeds of the same plant variety which lack the recombinant expression cassette. Other traits such as protein content, carbohydrate content, and oil content can be altered in the same manner.

Definitions

The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role.

The term "promoter" refers to a region or sequence determinants located upstream or downstream from the start of transcription and which are involved in recognition and binding of RNA polymerase and other proteins to initiate transcription. A "plant promoter" is a promoter capable of initiating transcription in plant cells.

The term "plant" includes whole plants, plant organs (e.g., leaves, stems, flowers, roots, etc.), seeds and plant cells and progeny of same. The class of plants which can be used in the method of the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is different from any naturally occurring allelic variants. As defined here, a modified ADC coding sequence which is heterologous to an operably linked ADC promoter does not include the T-DNA insertional mutants (e.g., ap2–10) as described in Jofuku et al. *The Plant Cell* 6:1211–1225 (1994).

A polynucleotide "exogenous to" an individual plant is a polynucleotide which is initially introduced into the plant by any means other than by a sexual cross. Examples of means by which this can be accomplished are described below, and include *Agrobacterium*-mediated transformation, biolistic methods, electroporation, and the like. Such a plant containing the exogenous nucleic acid is referred to here as an $R_1$ generation transgenic plant. Transgenic plants which arise from sexual cross or by selfing are descendants of such a plant.

An "ADC (AP2 domain containing) nucleic acid" or "ADC polynucleotide sequence" of the invention is a subsequence or full length polynucleotide sequence of a gene which, encodes an polypeptide containing an AP2 domain. A class of these nucleic acids encode polypeptides which, when present in a transgenic plant, can be used to modulate seed properties in seed produced by the plant. Native ADC polynucleotides are defined by their ability to hybridize under defined conditions to the exemplified nucleic acids or PCR products derived from them. An ADC polynucleotide (e.g., those shown in the Sequence Listing) is typically at least about 30–40 nucleotides to about 3000, usually less than about 5000 nucleotides in length. Usually the nucleic acids are from about 100 to about 2000 nucleotides, often from about 500 to about 1700 nucleotides in length.

ADC nucleic acids, as explained in more detail below, are a class of plant regulatory genes that encode ADC polypeptides, which are distinguished by the presence of one or more of a repeated amino acid repeated motif, referred to here as the "AP2 domain". Typically, such a motif is at least 50 amino acids; more typically, at least 54 amino acids; even more typically, at least 56, 59, 62, 65, or 68 amino acids in length. The scope of the invention includes native ADC nucleic acids, allelic variants, and other variants, such as mutants, fragments, and fusions.

ADC polypeptides includes those native oat, wheat, rice, and corn sequences disclosed in the Sequence Listing.

One of skill will recognize that in light of the present disclosure various modifications (e.g., substitutions, additions, and deletions) can be made to the sequences shown there without substantially affecting its function. These variations are specifically covered by the terms ADC polypeptide or ADC polynucleotide.

An "allelic variant" is a sequence that is a variant of native polynucleotides shown in the Sequence Listing, but represents the same chromosomal locus in the organism. In addition to those which occur by normal genetic variation in a population and perhaps fixed in the population by standard breeding methods, allelic variants can be produced by genetic engineering methods. A preferred allelic variant is one that is found in a naturally occurring plant, including a laboratory strain. Allelic variants are either silent or expressed. A silent allele is one that does not affect the phenotype of the organism. An expressed allele results in a detectable change in the phenotype of the trait represented by the locus. Alleles can occur in any portion of the genome, including regulatory regions as well as structural genes.

In the case of both expression of transgenes and inhibition of endogenous genes (e.g., by antisense, or sense suppression) one of skill will recognize that the inserted polynucleotide sequence need not be identical, but may be only "substantially identical" to a sequence of the gene from which it was derived. As explained below, these substantially identical variants are specifically covered by the term ADC nucleic acid.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the terms "ADC nucleic acid." In addition, the term specifically includes those full length sequences substantially identical (determined as described below) with an ADC polynucleotide sequence and that encode proteins that retain the function of the ADC polypeptide (e.g., resulting from conservative substitutions of amino acids in the AP2 polypeptide). In addition, variants can be those that encode dominant negative mutants as described below.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the complementary sequence is identical to all or a portion of a reference polynucleotide sequence.

Sequence comparisons between two (or more) polynucleotides or polypeptides are typically performed by comparing sequences of the two sequences over a "comparison window" to identify and compare local regions of sequence similarity. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (*U.S.A.*) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection. If GAP and BESTFIT are employed to determine optimal alignment, typically, the default values of 5.00 for gap weight and 0.30 for gap weight length are used.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least about 60% sequence identity, preferably at least about 80%, more preferably at least about 85% and most preferably, at least about 90, 92%, 95%, 98%, of 99% compared to a reference sequence using the programs described above (preferably BLAST) using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least about 35%, preferably at least about 60%, more preferably at least about 70% or about 80%, and most preferably at least about 90, 92%, 95%, 98%, of 99%. Polypeptides which are "substantially similar" share sequences as noted above except that residue positions which are not identical may differ by conservative amino acid changes. Conservative amino acid substitutions refer to the interchangeability of residues having similar side chains.

For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Another indication that nucleotide sequences are substantially identical is if two molecules hybridize to each other, or a third nucleic acid, under stringent conditions. Stringent conditions are sequence dependent and will be different in different circumstances. Usually, stringent conditions are selected to be about 15° C. lower than the thermal melting point (Tm) for the specific sequence at a defined ionic strength and pH; more usually, about 10° C. lower; even more usually, about 9° C., 7° C. or 5° C. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C.

In the present invention, genomic DNA or cDNA comprising ADC nucleic acids of the invention can be identified in standard Southern blots under stringent conditions using the nucleic acid sequences disclosed here. For the purposes of this disclosure, stringent conditions for such hybridizations are those which include at least one wash in 0.2×SSC at a temperature of at least about 50° C., usually about 55° C. to about 60° C., for 20 minutes, or equivalent conditions. Other means by which nucleic acids of the invention can be identified are described in more detail below.

DESCRIPTION OF THE PREFERRED EMBODIMENTS

This invention relates to plant ADC genes, such as those from oat, wheat, rice, and corn. The invention provides molecular strategies for controlling seed size and total seed protein using ADC overexpression and antisense gene constructs. In particular, transgenic plants containing antisense constructs have dramatically increased seed mass, seed protein, or seed oil. Alternatively, overexpression of ADC using a constructs of the invention leads to reduced seed size and total seed protein. Together, data presented here demonstrate that a number of agronomically important traits including seed mass, total seed protein, and oil content, can be controlled in species of agricultural importance.

Isolation of ADC Nucleic Acids

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., (1989).

The isolation of ADC nucleic acids may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as flowers, and a cDNA library which contains the ADC gene transcript is prepared from the mRNA. Alternatively, cDNA may be prepared from mRNA extracted from other tissues in which ADC genes or homologs are expressed.

The cDNA or genomic library can then be screened using a probe based upon the sequence of a cloned ADC gene disclosed here. Probes may be used to hybridize with genomic DNA or cDNA sequences to isolate homologous genes in the same or different plant species. Alternatively, antibodies raised against an ADC polypeptide can be used to screen an mRNA expression library.

Alternatively, the nucleic acids of interest can be amplified from nucleic acid samples using amplification techniques. For instance, polymerase chain reaction (PCR) technology can be used to amplify the sequences of the ADC genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying ADC sequences from plant tissues are generated from comparisons of the sequences provided in Jofuku et al., supra or in Bouckaert et al., Ser. No. 60/121,700, filed 25 Feb. 1999. For a general overview of PCR see *PCR Protocols: A Guide to Methods and Applications*. (Innis, M, Gelfand, D., Sninsky, J. and White, T., eds.), Academic Press, San Diego (1990).

As noted above, the nucleic acids of the invention are characterized by the presence of sequence encoding an AP2 domain or fragments thereof. Thus, these nucleic acids can be identified by their ability to specifically hybridize to sequences encoding AP2 domain disclosed here. Primers which specifically amplify AP2 domains of the exemplified genes are particularly useful for identification of particular ADC polynucleotides. Primers suitable for this purpose based on the sequences of the Sequence Listing. The PCR primers are used under standard PCR conditions (described for instance in Innis et al.) using the nucleic acids as described above as a template. The PCR products generated by any of the reactions can then be used to identify nucleic acids of the invention (e.g., from a cDNA library) by their ability to hybridize to these products. Particularly preferred hybridization conditions use a Hybridization Buffer consisting of: 0.25M Phosphate Buffer (pH 7.2), 1 mM EDTA, 1% Bovine Serum Albumin, 7% SDS. Hybridization is then followed by a first wash with 2.0×SSC+0.1% SDS or 0.39M Na+ (Wash Buffer A) and subsequent washes with 0.2× SSC+0.1% SDS or 0.042M Na+ (Wash Buffer B). Hybridization temperature will be from about 45° C. to about 78° C., usually from about 50° C. to about 70° C. Followed by washes at 18° C.

Particularly preferred hybridization conditions are as follows:

| Hybridization Temp | Hybrid. Time | Wash Buffer A | Wash Buffer B |
|---|---|---|---|
| 78 degrees C. | 48 hrs | 18 degrees C. | 18 degrees C. |
| 70 degrees C. | 48 hrs | 18 degrees C. | 18 degrees C. |
| 65 degrees C. | 48 hrs | 18 degrees C. | 18 degrees C. |
| 60 degrees C. | 72 hrs | 18 degrees C. | 18 degrees C. |
| 55 degrees C. | 96 hrs | 18 degrees C. | 18 degrees C. |
| 45 degrees C. | 200 hrs | 18 degrees C. | No wash |

If desired, primers that amplify regions more specific to particular ADC genes can be used. The PCR products produced by these primers can be used in the hybridization conditions described above to isolate nucleic acids of the invention.

Polynucleotides may also be synthesized by well-known techniques as described in the technical literature. See, e.g., Carruthers et al., *Cold Spring Harbor Symp. Quant. Biol.* 47:411–418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

Standard nucleic acid hybridization techniques using the conditions disclosed above can then be used to identify full length cDNA or genomic clones.

In addition, the DNA primers based on the sequences shown in the Sequence Listing can be used in an inverse PCR reaction to specifically amplify flanking AP2 gene sequences. Such a technique is single primer PCR (SPPCR). A typical SPPCR reaction is as follows: 1–5 μg of template plant DNA, 10 pmol of a selected primer, and 1.25 U of Taq DNA polymerase in standard 1×PCR reaction buffer as specified by the manufacturer (Promega, Madison, Wis.). PCR reaction conditions of twenty (20) cycles of denaturation at 94° C. for 30 sec., primer-template annealing at 55° C. for 30 sec., synthesis at 72° C. for 1 min., 30 sec., two cycles (2) of denaturation at 94° C. for 30 sec., primer-template annealing at 30° C. for 15 sec., 35° C. for 15 sec., 40° C. for 15 sec., 45° C. for 15 sec., 50° C. for 15 sec., 55° C. for 15 sec., 60° C. for 15 sec., 65° C. for 15 sec., and synthesis at 72° C. for 1 min., 30 sec., thirty (30) cycles of denaturation at 94° C. for 30 sec., primer-template annealing at 55° C. for 30 sec., synthesis at 72° C. for 1 min., 30 sec., followed by one (1) cycle of prolonged synthesis at 72° C. for 7 min.

Other techniques for isolating native sequences that flank those shown in the Sequence Listing are described in Lee et al, WO9844161A1, a RT-PCR technique; Fehr et al., *Brain Res Brain Res Protoc* 3(3):242–51 (January 1999), a rapid amplification of cDNA ends (RACE) technique; Frohman et al., *Proc Natl Acad Sci USA* 85(23):8998–9002 (December 1988); and Uematsu et al., *Immunogenetics* 34(3):174–8 (1991).

Control of ADC Activity or Gene Expression

One of skill will recognize that a number of methods can be used to modulate ADC activity or gene expression. ADC activity can be modulated in the plant cell at the gene, transcriptional, posttranscriptional, translational, or posttranslational. Techniques for modulating ADC activity at each of these levels are generally well known to one of skill and are discussed briefly below.

Methods for introducing genetic mutations into plant genes are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, for example, X-rays or gamma rays can be used. Desired mutants are selected by assaying for increased seed mass, oil content and other properties.

Alternatively, homologous recombination can be used to induce targeted gene disruptions by specifically deleting or altering the ADC gene in vivo (see, generally, Grewal and Klar, *Genetics* 146: 1221–1238 (1997) and Xu et al., *Genes Dev.* 10: 2411–2422 (1996)). Homologous recombination has been demonstrated in plants (Puchta et al., *Experientia* 50: 277–284 (1994), Swoboda et al., *EMBO J.* 13: 484–489 (1994); and Offringa et al., *Proc. Natl. Acad. Sci. USA* 90: 7346–7350 (1993)).

In applying homologous recombination technology to the genes of the invention, mutations in selected portions of an ADC gene sequences (including 5' upstream, 3' downstream, and intragenic regions) such as those disclosed here are made in vitro and then introduced into the desired plant using standard techniques. Since the efficiency of homologous recombination is known to be dependent on the vectors used, use of dicistronic gene targeting vectors as described by Mountford et al. *Proc. Natl. Acad. Sci. USA* 91: 4303–4307 (1994); and Vaulont et al. *Transgenic Res.* 4: 247–255 (1995) are conveniently used to increase the efficiency of selecting for altered ADC gene expression in transgenic plants. The mutated gene will interact with the target wild-type gene in such a way that homologous recombination and targeted replacement of the wild-type gene will occur in transgenic plant cells, resulting in suppression of ADC activity.

Alternatively, oligonucleotides composed of a contiguous stretch of RNA and DNA residues in a duplex conformation with double hairpin caps on the ends can be used. The RNA/DNA sequence is designed to align with the sequence of the target ADC gene and to contain the desired nucleotide change. Introduction of the chimeric oligonucleotide on an extrachromosomal T-DNA plasmid results in efficient and specific ADC gene conversion directed by chimeric molecules in a small number of transformed plant cells. This method is described in Cole-Strauss et al. *Science* 273: 1386–1389 (1996) and Yoon et al. *Proc. Natl. Acad. Sci. USA* 93: 2071–2076 (1996).

Gene expression can be inactivated using recombinant DNA techniques by transforming plant cells with constructs comprising transposons or T-DNA sequences. ADC mutants prepared by these methods are identified according to standard techniques. For instance, mutants can be detected by PCR or by detecting the presence or absence of ADC mRNA, e.g., by Northern blots. Mutants can also be selected by assaying for increased seed mass, oil content and other properties.

The isolated nucleic acid sequences prepared as described herein, can also be used in a number of techniques to control endogenous ADC gene expression at various levels. Subsequences from the sequences disclosed here can be used to control, transcription, RNA accumulation, translation, and the like.

A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense suppression can act at all levels of gene regulation including suppression of RNA translation (see, Bourque *Plant Sci.* (*Limerick*) 105: 125–149 (1995); Pantopoulos In Progress in Nucleic Acid Research and Molecular Biology, Vol. 48. Cohn, W. E. and K. Moldave (Ed.). Academic Press, Inc.: San Diego, Calif., USA; London, England, UK. p. 181–238; Heiser et al. *Plant Sci.* (*Shannon*) 127: 61–69 (1997)) and by preventing the accumulation of mRNA which encodes the protein of interest, (see, Baulcombe *Plant Mol. Bio.* 32:79–88 (1996); Prins and Goldbach *Arch. Virol.* 141: 2259–2276 (1996); Metzlaff et al. *Cell* 88: 845–854 (1997), Sheehy et al., *Proc. Nat. Acad. Sci. USA,* 85:8805–8809 (1988), and Hiatt et al., U.S. Pat. No. 4,801,340).

The nucleic acid segment to be introduced generally will be substantially identical to at least a portion of the endogenous ADC gene or genes to be repressed. The sequence, however, need not be perfectly identical to inhibit expression. The vectors of the present invention can be designed such that the inhibitory effect applies to other genes within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of about 500 to about 1700 nucleotides is especially preferred.

A number of gene regions can be targeted to suppress ADC gene expression. The targets can include, for instance, the coding regions (e.g., regions flanking the PA2 domains), introns, sequences from exon/intron junctions, 5' or 3' untranslated regions, and the like. In some embodiments, the constructs can be designed to eliminate the ability of regulatory proteins to bind to ADC gene sequences that are required for its cell- and/or tissue-specific expression. Such transcriptional regulatory sequences can be located either 5'-, 3'-, or within the coding region of the gene and can be either promote (positive regulatory element) or repress (negative regulatory element) gene transcription. These sequences can be identified using standard deletion analysis, well known to those of skill in the art. Once the sequences are identified, an antisense construct targeting these sequences is introduced into plants to control AP2 gene transcription in particular tissue, for instance, in developing ovules and/or seed.

Oligonucleotide-based triple-helix formation can be used to disrupt ADC gene expression. Triplex DNA can inhibit DNA transcription and replication, generate site-specific mutations, cleave DNA, and induce homologous recombination (see, e.g., Havre and Glazer *J. Virology* 67:7324–7331 (1993); Scanlon et al. *FASEB J.* 9:1288–1296 (1995); Giovannangeli et al. *Biochemistry* 35:10539–10548 (1996); Chan and Glazer *J. Mol. Medicine* (*Berlin*) 75: 267–282 (1997)). Triple helix DNAs can be used to target the same sequences identified for antisense regulation.

Catalytic RNA molecules or ribozymes can also be used to inhibit expression of ADC genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. Thus, ribozymes can be used to target the same sequences identified for antisense regulation.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, *solanum nodiflorum* mottle virus and subterranean clover mottle virus. The design and use of target RNA-specific ribozymes is described in Zhao and Pick *Nature* 365:448–451 (1993); Eastham and Ahlering *J. Urology* 156:1186–1188 (1996); Sokol and Murray *Transgenic Res.* 5:363–371 (1996); Sun et al. *Mol. Biotechnology* 7:241–251 (1997); and Haseloff et al. *Nature,* 334:585–591 (1988).

Another method of suppression is sense cosuppression. Introduction of nucleic acid configured in the sense orientation has been recently shown to be an effective means by which to block the transcription of target genes. For an example of the use of this method to modulate expression of endogenous genes (see, Assaad et al. *Plant Mol. Bio.* 22: 1067–1085 (1993); Flavell *Proc. Natl. Acad. Sci. USA* 91: 3490–3496 (1994); Stam et al. *Annals Bot.* 79: 3–12 (1997); Napoli et al., *The Plant Cell* 2:279–289 (1990); and U.S. Pat. Nos. 5,034,323, 5,231,020, and 5,283,184).

The suppressive effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used. In addition, the same gene regions noted for antisense regulation can be targeted using cosuppression technologies.

Alternatively, ADC activity may be modulated by eliminating the proteins that are required for ADC cell-specific gene expression. Thus, expression of regulatory proteins and/or the sequences that control ADC gene expression can be modulated using the methods described here.

Another method is use of engineered tRNA suppression of ADC mRNA translation. This method involves the use of suppressor tRNAs to transactivate target genes containing premature stop codons (see, Betzner et al. *Plant J.* 11:587–595 (1997); and Choisne et al. *Plant J.* 11: 597–604 (1997). A plant line containing a constitutively expressed ADC gene that contains an amber stop codon is first created. Multiple lines of plants, each containing tRNA suppressor gene constructs under the direction of cell-type specific promoters are also generated. The tRNA gene construct is then crossed into the ADC line to activate ADC activity in a targeted manner. These tRNA suppressor lines could also be used to target the expression of any type of gene to the same cell or tissue types.

Some ADC proteins (e.g., AP2) are believed to form multimers in vivo. As a result, an alternative method for inhibiting ADC function is through use of dominant negative mutants. This approach involves transformation of plants with constructs encoding mutant ADC polypeptides that form defective multimers with endogenous wild-type ADC proteins and thereby inactivate the protein. The mutant polypeptide may vary from the naturally occurring sequence at the primary structure level by amino acid substitutions, additions, deletions, and the like. These modifications can be used in a number of combinations to produce the final modified protein chain. Use of dominant negative mutants to inactivate target genes is described in Mizukami et al. *Plant Cell* 8:831–845 (1996). DNA sequence analysis and DNA binding studies strongly suggests that ADC polypeptides can function as transcription factors. See, for example, (Jofuku et al., *Plant Cell* 6: 1211–1225 (1994). Thus, dominant-negative forms of ADC genes that are defective in their abilities to bind to DNA can also be used.

The native ADC proteins may exist in both a phosphorylated and a nonphosphorylated form. Thus, activity may also be regulated by protein kinase signal transduction cascades. In addition, such genes may be regulated by and/or play a role in protein kinase signal transduction cascades (EREBPs, Ohme-Takagi and Shinshi *Plant Cell* 7: 173–182 (1995); AtEBP, Buttner and Singh *Proc. Natl. Acad. Sci. USA* 94: 5961–5966 (1997); Pti4/5/6, Zhou et al. *EMBO J.* 16: 3207–3218 (1997)). Thus, mutant forms of the ADC proteins used in dominant negative strategies can include substitutions at amino acid residues targeted for phosphorylation so as to decrease phosphorylation of the protein. Alternatively, the mutant ADC forms can be designed so that they are hyperphosphorylated.

Glycosylation events are known to affect protein activity in a cell- and/or tissue-specific manner (see, Meshi and Iwabuchi *Plant Cell Physiol.* 36: 1405–1420 (1995); Meynial-Salles and Combes *J. Biotech.* 46: 1–14 (1996)). Thus, mutant forms of the ADC proteins can also include those in which amino acid residues that are targeted for glycosylation are altered in the same manner as that described for phosphorylation mutants.

ADC polypeptide may carry out some of its functions through its interactions with other transcription factors/proteins (e.g., AINTEGUMENTA, Elliott et al. *Plant Cell* 8: 155–168 (1996); Klucher et al. *Plant Cell* 8: 137–153 (1996); CURLY LEAF, Goodrich et al. *Nature* (*London*) 386: 44–51 (1997); or LEUNIG, Liu and Meyerowitz *Development* 121: 975–991 (1995). Thus, one simple method for suppressing ADC activity is to suppress the activities of proteins that are required for ADC activity. ADC activity can thus be controlled by "titrating" out transcription factors/ proteins required for ADC activity. This can be done by overexpressing domains ADC proteins that are involved in protein:protein interactions in plant cells (e.g., AP2 domains or the putative transcriptional activation domain as described in Jofuku et al., *Plant Cell* 6: 1211–1225 (1994)). This strategy has been used to modulate gene activity (Lee et al., *Exptl. Cell Res.* 234: 270–276 (1997); Thiesen *Gene Expression* 5: 229–243 (1996); and Waterman et al., *Cancer Res.* 56: 158–163 (1996)).

Another strategy to affect the ability of an ADC protein to interact with itself or with other proteins involves the use of antibodies specific to ADC. In this method cell-specific expression of AP2-specific Abs is used inactivate functional domains through antibody:antigen recognition (see, Hupp et al. *Cell* 83:237–245 (1995)).

Use of Nucleic Acids of the Invention to Enhance ADC Gene Expression

Isolated sequences prepared as described herein can also be used to introduce expression of a particular ADC nucleic acid to enhance or increase endogenous gene expression. Enhanced expression will generally lead to smaller seeds or seedless fruit. Where overexpression of a gene is desired, the desired gene from a different species may be used to decrease potential sense suppression effects.

One of skill will recognize that the polypeptides encoded by the genes of the invention, like other proteins, have different domains which perform different functions. Thus, the gene sequences need not be full length, so long as the desired functional domain of the protein is expressed. The distinguishing features of ADC polypeptides, including the AP2 domain, are discussed in detail below.

Modified protein chains can also be readily designed utilizing various recombinant DNA techniques well known to those skilled in the art and described in detail, below. For example, the chains can vary from the naturally occurring sequence at the primary structure level by amino acid substitutions, additions, deletions, and the like. These modifications can be used in a number of combinations to produce the final modified protein chain.

Variant of Native ADC Polypeptides

Polypeptide variants of the native ADC sequences shown in the Sequence Listing and the polynucleotides that encode such variants are within the scope of the invention.

Variants, including mutants, fragments, and fusions will exhibit at least about 35% sequence identity to those native polypeptides shown in the Sequence Listing or fragments thereof, more typically, at least about 60%; even more typically, at least about 70%. Sequence identity is used for polypeptides as defined above for polynucleotides. More preferably, the variants will exhibit at least about 85% sequence identity; even more preferably, at least about 90% sequence identity; more preferably at least about 95%, 96%, 97%, 98%, or 99% sequence identity.

Furthermore, the variants will exhibit at least one of the structural properties of a native ADC protein. Such structural properties include, without limitation, 3-dimensional structure, serine-rich acidically charged regions and alpha-helical structure.

Furthermore, variants are functional, in that variants exhibit at least one of the activities of the native protein. Such activities include, without limitation, protein—protein interaction, DNA interaction, biological activity, immunological activity, signal transduction activity, transcription activity, etc. More specifically, the activities include DNA binding, activation of transcription or transcription factors, multimer formation, nuclear localization, and as a substrate for phosphorylation or glycosylation. Typically, the variants are capable of exhibiting at least about 60% of the activity of the native protein; more typically, about 70%; even more typically, at least about 80%, 85%, 90% or 95% of at least one activity of the native protein.

Mutants of the native polypeptides comprise amino acid additions, deletions, or substitutions. "Conservative substitutions" are preferred to maintain the function or activity of the polypeptide. Such substitutions include conservation of charge, polarity, hydrophobicity, size, etc. For example, one or more amino acid residues within the sequence can be substituted with another amino acid of similar polarity that acts as a functional equivalent, for example providing a hydrogen bond in an enzymatic catalysis. Substitutes for an amino acid within an exemplified sequence are preferably made among the members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Other examples of conservative substitutions are described above.

Fragments of the native and mutant polypeptides of the invention comprise deletion of the amino acids at either termini. Fragments of particular interest are those that include only one of domains included in the native ADC polypeptides. Further, fusions of native polypeptides, mutants, and fragment, can comprise additional individual amino acids or amino acid sequences inserted into the polypeptide in the middle thereof and/or at the N-terminal and/or C-terminal ends thereof. Chimeras can be constructed of fragments of the instant invention and other ADC sequences, such as *Arabidopsis* AP2 and RAP2 genes. In addition, chimeras comprising fragment of the instant ADC polypeptides with domains from other transcription factors are of interest. For example, a leucine zipper can be fused to an ADC sequence.

The native ADC polypeptides of the instant invention, comprising sequences shown in the Sequence Listing, comprise a number of domains, elements, regions, and motifs. To construct a variant that retains or exhibits enhanced ADC polypeptide activities, either no changes or conservative substitutes are made to any one of the domains, elements, regions, or motifs. Typically, changes can be made to the amino acids that flank the domains, elements, regions, and/or motifs without disrupting ADC activity.

To construct dominant negative mutants, or variants that lack one of the native ADC activities, changes to the native sequences can be made within the domains, elements, and regions described below. Such changes can disrupt either the secondary structure, charge nature, or hydrophobicity of the unaltered domains, elements, or regions to render a variant with diminished ADC activity.

Native ADC polypeptides of the invention can include any one of the following domains, elements, regions, or motifs:

(a) serine-rich acidic domain;
(b) nuclear localization motif;
(c) AP2 domain;
(d) YRD element;
(e) RAYD element;
(f) WEAR/WESH;
(g) WAAEIRD motif;

(h) Linker; and (i) Carboxyl terminal tail.

Some of the native polypeptides of the invention can comprise an amino terminal serine-rich acidic domain. Such a domain can be identified by sequence similarity to the serine-rich acidic domain in *Arabidopsis* AP2, amino acids 14–50, as numbered in copending application U.S. Ser. No. 09/026,039, filed Feb. 19, 1998. This domain is analogous to regions that function as activation domains in a number of RNA polymerase transcription factors. Consequently, changes to this region can modulate activation activity of a variant. Such a domain within a variant can be either longer or shorter than those included in a native protein. Typically, such a domain, modified or unmodified as compared to the native, is at least about 20 amino acids; more typically, at least about 25 amino acids; even more typically, at least about 30 amino acids; even more typically, at least about 37 amino acids.

In addition, a highly basic amino acid domain with a lysine-lysine-serine-arginine "KKSR" motif capable of nuclear localization of the polypeptide can be included in the native polypeptide sequences of the invention. If nuclear localization is undesired in a variant, such a domain can be deleted or modified to diminish activity. This domain or modification of those found in the native protein can be utilized to enhance or retain activity. Typically, such a domain is at least about 4 amino acids; more typically, at least about 7 amino acids; even more typically, at least about 10 amino acids.

All native ADC polypeptides of the invention include at least one AP2 domain, some can include two domains. Both copies of this domain or core region are capable of forming amphipathic α-helical structures. This domain can be responsible for conferring DNA binding or multimer formation or protein—protein interaction activities.

Two blocks are found within each AP2 domain. The first block, referred to as the YRG element, is highly basic and contains the conserved tyrosine-arginine-glycine referred to as YRG (tyrosine-arginine-glycine) amino acid motif. This element can be involved in DNA binding. Either insertion or substitution of acidic residues or deletions of basic residues in this region can diminish the binding activity. In addition, activity can be disrupted by removing or substituting amino acids in the YRG motif. To retain or enhance such DNA binding activity conservative substitutions or no changes are made to this element. A modified element can be included in a variant that is longer or shorter than the element in a native ADC polypeptide. Typically, the length is between at least about 15 amino acids; more typically, at least about 19 amino acids; even more typically, at least about 22 amino acids.

An AP2 domain also includes a second block of amino acids, referred to herein as the RAYD element (arginine-alanine-tyrosine-aspartic acid). This element is capable of forming an amphipathic alpha helix with alternating charges. This element can be responsible for DNA binding, multimer formation, or protein—protein interaction. Disruption or diminishment of these activities can be occur when either;

(1) the domain is altered so an alpha-helix cannot be formed, such as an inclusion of a proline residue; or (2) altering the hydrophobicity or charge of the alpha-helix.

To retain or enhance the recited activities, the either no changes or conservative substitutions are made to the native sequence; specifically, in the RAYD motif. Typically, such a element, whether unchanged or modified from the native sequence is at least about 35 amino acids; more typically, at least about 40 amino acid; even more typically, about 42, 43, or 44 amino acids in length. The core region within the RAYD element is predicted to form an amphipathic alpha helix. Typically, this core region is about 12 amino acids; more typically, about 15 amino acids; even more typically, about 18 amino acids in length.

In addition, several invariant amino acid residues within the YRG and RAYD elements that may also play a role in the structure or function of these ADC proteins. For example, glycine residue at position 40 within the RAYD elements is invariant in all AP2 domain containing proteins, and has been shown to be important for AP2 function (Jofuku et al., *Plant Cell* 6: 1211–1225 (1994)). This glycine is at position 1 of all the polypeptides sequences in the Sequence Listing. Mutation of this glycine can result in a variant that is able to act as a double negative mutant.

To retain and enhance activity, polypeptides comprising two AP2 domains, can contain a conserved WEAR/WESH amino acid sequence motif located in the YRG element of both AP2 domain repeats. Diminishment or reduction of ADC activity can result in variants that do not include a WEAR or WESH motif.

Alternatively, variant polypeptides with only one AP2 domain can possess a conserved 7-maino acid sequence motif referred to as the WAAEIRD box in place of the WEAR/WESH motif located in the YRG element.

Conservation of serine residues in the YRG and RAYD elements is preferred when phosphorylation is desired. Substitution of these serines can change the phosphorylation pattern and therefore change the activity of the variant.

Phosphorylation of native polypeptides results in a negatively charged residue. This change in charge can lead to changes in activity. Thus, inclusion of negatively charged residues can modulate the activity exhibited by a variant polypeptide.

Spacing between two AP2 domains can be a factor in retaining or enhancing activity. Typically, the linker region is at least about 20, 22, 24, 25 or 26 amino acids in length. Examples of the conserved amino acid sequence are shown in Klucher et al., *Plant Cell* 8: 137–153 (1996); and in Okamuro et al., *Proc. Natl. Acad. Sci. USA* 94: 7076–7081 (June 1997).

The full-length native sequences can comprise a carboxyl terminal tail. In native polypeptides this tail can include motifs such as a string of negatively or positively charged residues. One example is a poly-glutamine motif, which is usually, at least about 3 amino acids; more usually, at least about 4 amino acids.

One class of mutants of interest are those that have additions, substitutions, and deletions in the sequences flanking the domains described above. Further, fragments comprising the domains described above are of interest also. Fusions of such fragments with other AP2 and RAP2 genes, of *Arabidopsis*, for example, are included within the invention.

Preparation of Recombinant Vectors

To use isolated sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22:421–477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill. Such genes include for example, the AP2 gene, ACT11 from *Arabidopsis* (Huang et al. *Plant Mol. Biol.* 33:125–139 (1996)), Cat3 from *Arabidopsis* (GenBank No. U43147, Zhong et al., *Mol. Gen. Genet.* 251:196–203 (1996)), the gene encoding stearoyl-acyl carrier protein desaturase from *Brassica napus* (Genbank No. X74782, Solocombe et al. *Plant Physiol.* 104:1167–1176 (1994)), GPc1 from maize (GenBank No. X15596, Martinez et al. *J. Mol. Biol* 208:551–565 (1989)), and Gpc2 from maize (GenBank No. U45855, Manjunath et al., *Plant Mol. Biol.* 33:97–112 (1997)).

Alternatively, the plant promoter may direct expression of the ADC nucleic acid in a specific tissue or may be otherwise under more precise environmental or developmental control. Examples of environmental conditions that may effect transcription by inducible promoters include anaerobic conditions, elevated temperature, or the presence of light. Such promoters are referred to here as "inducible" or "tissue-specific" promoters. One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

Examples of promoters under developmental control include promoters that initiate transcription only (or primarily only) in certain tissues, such as fruit, seeds, or flowers. Promoters that direct expression of nucleic acids in ovules, flowers or seeds are particularly useful in the present invention. As used herein a seed-specific promoter is one which directs expression in seed tissues, such promoters may be, for example, ovule-specific, embryo-specific, endosperm-specific, integument-specific, seed coat-specific, or some combination thereof. Examples include a promoter from the ovule-specific BEL1 gene described in Reiser et al. *Cell* 83:735–742 (1995)(GenBank No. U39944). Other suitable seed specific promoters are derived from the following genes: MAC1 from maize (Sheridan et al. *Genetics* 142:1009–1020 (1996), Cat3 from maize (GenBank No. L05934, Abler et al. *Plant Mol. Biol.* 22:10131–1038 (1993), the gene encoding oleosin 18 kD from maize (GenBank No. J05212, Lee et al. *Plant Mol. Biol.* 26:1981–1987 (1994)), vivparous-1 from *Arabidopsis* (Genbank No. U93215), the gene encoding oleosin from *Arabidopsis* (Genbank No. Z17657), Atmyc1 from *Arabidopsis* (Urao et al. *Plant Mol. Biol.* 32:571–576 (1996), the 2s seed storage protein gene family from *Arabidopsis* (Conceicao et al. *Plant* 5:493–505 (1994)) the gene encoding oleosin 20 kD from *Brassica napus* (GenBank No. M63985), napA from *Brassica napus* (GenBank No. J02798, Josefsson et al. *JBL* 26:12196–1301 (1987), the napin gene family from *Brassica napus* (Sjodahl et al. *Planta* 197:264–271 (1995), the gene encoding the 2S storage protein from *Brassica napus* (Dasgupta et al. *Gene* 133:301–302 (1993)), the genes encoding oleosin A (Genbank No. U09118) and oleosin B (Genbank No. U09119) from soybean and the gene encoding low molecular weight sulphur rich protein from soybean (Choi et al. *Mol Gen, Genet.* 246:266–268 (1995)).

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta.

Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment.

Microinjection techniques are known in the art and well described in the scientific and patent literature. The introduction of DNA constructs using polyethylene glycol precipitation is described in Paszkowski et al. *Embo J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:70–73 (1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al. *Science* 233:496–498 (1984), and Fraley et al. *Proc. Natl. Acad. Sci. USA* 80:4803 (1983).

Transformed plant cells which are derived by any of the above transformation techniques can be cultured to regenerate a whole plant which possesses the transformed genotype and thus the desired phenotype such as increased seed mass. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture, Handbook of Plant Cell Culture*, pp. 124–176, MacMillilan Publishing Company, New York, 1983; and Binding, *Regeneration of Plants, Plant Protoplasts*, pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

The nucleic acids of the invention can be used to confer desired traits on essentially any plant. Thus, the invention has use over a broad range of plants, including species from the genera *Anacardium, Arachis, Asparagus, Atropa, Avena,*

*Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna,* and *Zea.*

Increasing seed size, protein, amino acid, and oils content is particularly desirable in crop plants in which seed are used directly for animal or human consumption or for industrial purposes. Examples include soybean, canola, and grains such as rice, wheat, corn, rye, and the like. Decreasing seed size, or producing seedless varieties, is particularly important in plants grown for their fruit and in which large seeds may be undesirable. Examples include cucumbers, tomatoes, melons, and cherries.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Since transgenic expression of the nucleic acids of the invention leads to phenotypic changes in seeds and fruit, plants comprising the expression cassettes discussed above must be sexually crossed with a second plant to obtain the final product. The seed of the invention can be derived from a cross between two transgenic plants of the invention, or a cross between a plant of the invention and another plant. The desired effects (e.g., increased seed mass) are generally enhanced when both parental plants contain expression cassettes of the invention.

Seed obtained from plants of the present invention can be analyzed according to well known procedures to identify seed with the desired trait. Increased or decreased size can be determined by weighing seeds or by visual inspection. Protein content is conveniently measured by the method of Bradford et al. *Anal. Bioch.* 72:248 (1976). Oil content is determined using standard procedures such as gas chromatography. These procedures can also be used to determine whether the types of fatty acids and other lipids are altered in the plants of the invention.

Using these procedures one of skill can identify the seed of the invention by the presence of the expression cassettes of the invention and increased seed mass. Usually, the seed mass will be at least about 10%, often about 20% greater than the average seed mass of plants of the same variety that lack the expression cassette. The mass can be about 50% greater and preferably at least about 75% to about 100% greater. Increases in other properties e.g., protein and oil will usually be proportional to the increases in mass. Thus, in some embodiments protein or oil content can increase by about 10%, 20%, 50%, 75% or 100%, or in approximate proportion to the increase in mass.

Alternatively, seed of the invention in which AP2 expression is enhanced will have the expression cassettes of the invention and decreased seed mass. Seed mass will be at least about 20% less than the average seed mass of plants of the same variety that lack the expression cassette. Often the mass will be about 50% less and preferably at least about 75% less or the seed will be absent. As above, decreases in other properties e.g., protein and oil will be proportional to the decreases in mass.

The following Examples are offered by way of illustration, not limitation.

EXAMPLE 1

ADC Gene Isolation

The isolation and characterization of ADC genes of the instant invention from oat, wheat, rice, and maize are described also in detail in Bouckaert et al., U.S. Provisional Application No. 60/121,700.

Plant DNA

For this example, plant DNAs were isolated according to Jofuku and Goldberg (1988), "Analysis of plant gene structure," *In Plant Molecular Biology: A Practical Approach,* Shaw, ed. (Oxford:IRL Press), pages 37–66.

The plant DNAs were isolated from *Avena sativa, Triticum aestivum, Oryza sativa,* and *Zea mays.*

Oligonucleotides

Oligonucleotide primer pairs were selected from template *Arabidopsis* gene sequences using default parameters and the PrimerSelect 3.11 software program (Lasergene sequence analysis suite, DNASTAR, Inc., Madison, Wis.). Selected primer pairs were then used to generate PCR products utilizing genomic DNA from *Brassica napus* as a template. PCR products were either sequenced directly or cloned into *E. coli* using the TOPO™ TA vector cloning system according to manufacturer's guidelines (Invitrogen, Carlsbad, Calif.). Nucleotide sequences of PCR products and/or cloned inserts were determined using an ABI PRISM® 377 DNA Analyzer as specified by the manufacturer (PE Applied Biosystems, Foster City, Calif.) and compared to the template *Arabidopsis* gene sequence using default parameters and the SeqMan 3.61 software program (Lasergene sequence analysis suite, DNASTAR, Inc., Madison, Wis.). *Brassica napus* gene regions of greater than or equal to 17 nucleotides in length and 70% sequence identity relative to the *Arabidopsis* gene were selected and the nucleotide sequences translated into the corresponding amino acid sequences using standard genetic codes. Using the deduced amino acid sequences, the corresponding sequences of triplet codons of the *Arabidopsis* gene region, and genera- and/or species-specific codon usage tables, oligonucleotide primer pairs were designed for use in identifying similar gene regions that would encode identical peptides in various unrelated plant genera. In all cases, the DNA sequence of a primer or its reverse complement would be identical to the sequence of triplet codons of the *Arabidopsis* gene sequence at nucleotide positions 1 and 2. In some cases the nucleotide at position 3 of a triplet codon would be identical to the *Arabidopsis* codon if that codon is preferentially used in a given plant genera and/or species as determined by published codon usage tables. In other cases, position 3 would be selected (e.g., A, G, C, T) using genera- and/or species-specific codon usage tables such that the designated nucleotide together with nucleotides in positions 1 and 2 will form a triplet codon that will encode an amino acid that is identical to that encoded by the *Arabidopsis* triplet codon. In some of these cases, where there is an equal probability of using one codon or another that encodes the same amino acid but differs only at position 3, then the selection of an A, G, C, or T residue will not generate a string of homopolynucleotides greater than four (4) nucleotides.

PCR

A typical PCR reaction consisted of 1 μg of template plant DNA, 10 pmol of each primer of a selected primer pair, and 1.25 U of Taq DNA polymerase in standard 1×PCR reaction buffer as specified by the manufacturer (Promega, Madison, Wis.). PCR reaction conditions consisted of one (1) initial cycle of denaturation at 94° C. for 7 min, thirty-five (35) cycles of denaturation at 94° C. for 1 min., primer-template annealing at 58° C. for 30 sec., synthesis at 68° C. for 4 min., and one (1) cycle of prolonged synthesis at 68° C. for 7 min.

Identification of Gene Sequences

Specific products were extracted from agarose gels and either sequenced directly using the selected primer(s) as sequencing primers or first cloned into E. coli using the TOPO™ TA vector cloning system according to manufacturer's guidelines (Invitrogen, Carlsbad, Calif.) and cloned inserts sequenced using an ABI PRISM® 377 DNA Analyzer as specified by the manufacturer (PE Applied Biosystems, Foster City, Calif.).

Reference is made throughout this document to numerous articles of the scientific and patent literature. Each such article is hereby incorporated by reference in its entirety by citation.

What is claimed is:

1. A method of modulating seed mass in a plant, the method comprising:
   (a) providing a first plant comprising a recombinant expression cassette containing an ADC nucleic acid linked to a plant promoter, said ADC nucleic acid sequence comprising:
      (i) a nucleic acid sequence having at least 90% sequence identity to the nucleic acid sequence as set forth in SEQ ID NO: 1; or
      (ii) a nucleic acid sequence that encodes SEQ ID NO: 2;
   (b) selfing the first plant or crossing the first plant with a second plant, thereby producing at least one seed; and
   (c) selecting at least one seed with altered mass.

2. The method of claim 1, wherein the step of selecting includes the step of selecting seed with increased mass.

3. The method of claim 2, wherein the seed has increased protein content, carbohydrate content, or oil content.

4. The method of claim 2, wherein the ADC nucleic acid is linked to the plant promoter in the antisense orientation.

5. The method of claim 2, wherein the ADC nucleic acid comprises a nucleic acid sequence having at least 92% sequence identity to SEQ ID NO: 1.

6. The method of claim 2, wherein the ADC nucleic acid comprises a nucleic acid sequence having at least 95% sequence identity to SEQ ID NO:1.

7. The method of claim 2, wherein the ADC nucleic acid comprises a nucleic acid sequence having at least 98% sequence identity to SEQ ID NO: 1.

8. The method of claim 2, wherein the ADC nucleic acid is SEQ ID NO: 1.

9. The method of claim 2, wherein the first and second plants are the same species.

10. The method of claim 2, wherein the first and second plants are members of the family Brassicaceae.

11. The method of claim 2, wherein the first and second plants are members of the family Solanaceae.

12. The method of claim 2, wherein the plant promoter is a constitutive promoter.

13. The method of claim 12, wherein the promoter is a CaMV 35S promoter.

14. The method of claim 2, wherein the promoter is a tissue-specific promoter.

15. The method of claim 14, wherein the promoter is ovule-specific.

16. A seed produced by the method of claim 2, wherein the seed comprises said expression cassette.

17. The method of claim 1, wherein the step of selecting includes the step of selecting seed with decreased mass.

18. The method of claim 17, wherein the first and second plants are the same species.

19. The method of claim 17, wherein the first and second plants are members of the family Brassicaceae.

20. The method of claim 17, wherein the first and second plants are members of the family Solanaceae.

21. The method of claim 17, wherein the plant promoter is a constitutive promoter.

22. The method of claim 21, wherein the promoter is a CaMV 35S promoter.

23. The method of claim 17, wherein the promoter is a tissue-specific promoter.

24. The method of claim 23, wherein the promoter is ovule-specific.

25. A seed produced by the method of claim 17, wherein the seed comprises said expression cassette.

26. A seed comprising a recombinant expression cassette containing an ADC nucleic acid, said ADC nucleic acid sequence comprising:
   (i) a nucleic acid sequence having at least 90% sequence identity to the nucleic acid sequence as set forth in SEQ ID NO: 1; or
   (ii) a nucleic acid sequence that encodes SEQ ID NO: 2.

27. The seed of claim 26, which is derived from a plant that is a member of the family Brassicaceae.

28. The seed of claim 26, wherein the ADC nucleic acid comprises a nucleic acid having at least 92% sequence identity to the nucleic acid sequence as set forth in the SEQ ID NO: 1.

29. The seed of claim 26, wherein the ADC nucleic acid comprises a nucleic acid sequence having at least 95% identity to the nucleic acid sequence as set forth in SEQ ID NO: 1.

30. The seed of claim 26, wherein the ADC nucleic acid comprises a nucleic acid sequence having at least 98% identity to the nucleic acid sequence as set forth in SEQ ID NO: 1.

31. The seed of claim 26, wherein said ADC nucleic acid is linked to a plant promoter in an antisense orientation and the seed mass is at least about 10% greater than a seed from the same plant variety which lacks the recombinant expression cassette.

32. The seed of claim 31, wherein the mass is at least about 20% greater than a seed from the same plant variety which lacks the recombinant expression cassette.

33. The seed of claim 31, wherein the mass is at least about 50% greater than a seed from the same plant variety which lacks the recombinant expression cassette.

34. The seed of claim 31, wherein the oil content is at least 10% greater than a seed from the same plant variety which lacks the recombinant expression cassette.

35. The seed of claim 31, wherein the protein content is at least about 10% greater than a seed from the same plant variety which lacks the recombinant expression cassette.

36. The seed of claim 26, wherein said ADC nucleic acid is linked to a plant promoter in the sense orientation and the seed mass is at least about 10% less than a seed of the same plant variety which lacks the recombinant expression cassette.

37. The seed of claim 36, which has a mass at least about 20% less than a seed of the same plant variety which lacks the recombinant expression cassette.

38. The seed of claim 36, which has a mass at least about 50% less than a seed of the same plant variety which lacks the recombinant expression cassette.

39. A transgenic plant comprising an expression cassette containing a plant promoter operably linked to a heterologous ADC polynucleotide, wherein said ADC polynucleotide comprises:
   (i) a nucleic acid sequence having at least 90% sequence identity to SEQ ID NO: 1; or
   (ii) a nucleic acid sequence that encodes SEQ ID NO: 2.

40. The transgenic plant of claim 39, wherein the ADC polynucleotide comprises a nucleic acid sequence having at least 92% identity to the nucleic acid sequence as set forth in SEQ ID NO: 1.

41. The transgenic plant of claim 39, wherein the ADC polynucleotide comprises a nucleic acid sequence having at least 95% identity to the sequence as set forth in SEQ ID NO: 1.

42. The transgenic plant of claim 39, wherein the ADC polynucleotide comprises a nucleic acid sequence having at least 98% identity to the sequence as set forth in SEQ ID NO: 1.

43. The transgenic plant of claim 39, wherein the ADC polynucleotide comprises a nucleic acid sequence having at least 99% identity to the sequence as set forth in SEQ ID NO: 1.

44. The transgenic plant of claim 39, wherein said ADC polynucleotide is linked to the heterologous promoter in an antisense orientation.

45. The transgenic plant of claim 39, which is a member of the genus *Brassica*.

46. An isolated nucleic acid molecule comprising an expression cassette containing a plant promoter operably linked to a heterologous ADC polynucleotide, wherein said ADC polynucleotide comprises:
   (i) a nucleic acid sequence having at least 90% sequence identity to SEQ ID NO: 1; or
   (ii) a nucleic acid sequence that encodes SEQ ID NO: 2.

47. The isolated nucleic acid molecule of claim 46, wherein the ADC polynucleotide has a sequence having at least 92% identity to SEQ ID NO: 1.

48. The isolated nucleic acid molecule of claim 46, wherein the ADC polynucleotide comprises a nucleic acid sequence having at least 95% sequence identity to the nucleic acid sequence as set forth in SEQ ID NO: 1.

49. The isolated nucleic acid molecule of claim 46, wherein the ADC polynucleotide comprises a nucleic acid sequence having at least 98% sequence identity to the nucleic acid sequence as set forth in SEQ ID NO: 1.

50. The isolated nucleic acid of claim 46, wherein the ADC polynucleotide is linked to the heterologous promoter in an antisense orientation.

51. The isolated nucleic acid of claim 46, which is a member of the genus *Brassica*.

* * * * *